United States Patent
Oosawa et al.

(10) Patent No.: US 8,832,114 B2
(45) Date of Patent: Sep. 9, 2014

(54) CASE DATABASE MANAGEMENT SYSTEM AND METHOD

(75) Inventors: Akira Oosawa, Tokyo (JP); Takayuki Udagawa, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 1156 days.

(21) Appl. No.: 12/058,746

(22) Filed: Mar. 30, 2008

(65) Prior Publication Data

US 2008/0243886 A1 Oct. 2, 2008

(30) Foreign Application Priority Data

Mar. 30, 2007 (JP) ................................. 2007-095441

(51) Int. Cl.
*G06F 17/30* (2006.01)
(52) U.S. Cl.
USPC ............................ 707/748; 382/128; 382/224
(58) Field of Classification Search
CPC .................... G06F 17/30244; G06F 17/30265; G06F 17/30268; G06F 19/321
See application file for complete search history.

(56) References Cited

U.S. PATENT DOCUMENTS

| | | | |
|---|---|---|---|
| 5,019,975 A * | 5/1991 | Mukai ................................... | 1/1 |
| 8,184,916 B2 * | 5/2012 | Matraszek et al. ............ | 382/224 |
| 8,428,969 B2 * | 4/2013 | Hahn et al. ......................... | 705/3 |
| 2003/0144877 A1 * | 7/2003 | Goldmann et al. ............... | 705/2 |
| 2004/0167800 A1 * | 8/2004 | Chang et al. ...................... | 705/2 |
| 2005/0136549 A1 * | 6/2005 | Gholap et al. ................ | 436/501 |
| 2005/0177403 A1 * | 8/2005 | Johnson ............................. | 705/7 |
| 2005/0223045 A1 | 10/2005 | Funahashi et al. | |
| 2005/0234740 A1 * | 10/2005 | Krishnan et al. .................. | 705/2 |
| 2005/0256743 A1 * | 11/2005 | Dale ................................. | 705/2 |
| 2006/0274928 A1 * | 12/2006 | Collins et al. ................. | 382/132 |
| 2007/0292012 A1 * | 12/2007 | Brandon et al. ............. | 382/128 |
| 2008/0024520 A1 * | 1/2008 | Rudd ............................ | 345/619 |
| 2008/0120142 A1 * | 5/2008 | Jakobovits ........................ | 705/3 |

FOREIGN PATENT DOCUMENTS

JP 2005-284846 A 10/2005

* cited by examiner

*Primary Examiner* — Daniel Kinsaul
(74) *Attorney, Agent, or Firm* — Sughrue Mion, PLLC

(57) ABSTRACT

A case database management system capable of maintaining high quality case information registered in a case DB. A user of the case database management system can not only refer to case information registered in the case DB by user terminals, but also evaluate the case information. The case DB server of the system collects evaluation information evaluated by the user for each case information item and assigns each case information item with an evaluation containing an evaluation point indicating usefulness of the case information. This enables the case database management system to register more highly evaluated (high quality) case information in the case DB and to provide the user with useful case information.

12 Claims, 13 Drawing Sheets

FIG.2

| USER ID | NAME | PROFESSIONAL AFFILIATION | SPECIALTY | RANK |
|---|---|---|---|---|
| 2006155-35 | XX | XX UNIVERSITY SCHOOL OF MEDICINE | RADIOLOGY | 3.69 |
| 2006155-36 | YY | YY HOSPITAL | INTERNAL MEDICINE | 2.28 |
| ... | ... | ... | ... | ... |

FIG.3

| SUBSCRIBER | FLAT RATE | MEASURED RATE |
|---|---|---|
| INDIVIDUAL | XX YEN/ YEAR | XX YEN/ 1 ITEM |
| | XX YEN/ UP TO 100 ITEMS | |
| CORPORATE | XX YEN/ YEAR | XX YEN/ 1 ITEM |
| | XX YEN/ 10 LICENSES | |

FIG.8

EVALUATION BY USER (FIVE-POINT EVALUATION)
CLICK THE CHECK BOX ON THE LEFT OF AN ITEM.

COMMENT FIELD

☐5: VERY USEFUL
☐4: USEFUL
☐3: MIDDLE
☐2: NOT MUCH USEFUL
☐1: NOT USEFUL

FIG.9

| EVALUATION DATE | TIME | EVALUATION CASE ID | EVALUATOR ID | EVALUATION | SOURCE IP ADDRESS |
|---|---|---|---|---|---|
| 20060326 | 1427 | A0001-01 | 2006155-35 | 4 | 138.230.45.* |
| 20060326 | 1905 | A0001-01 | 2006258-02 | 2 | 144.150.24.* |
| 20060326 | 2315 | A0200-08 | 2004156-80 | 3 | 133.25.50.* |
| ... | ... | ... | ... | ... | ... |

FIG.11

| CASE ID | NUMBER OF EVALUATIONS | | | | | SCORE |
|---|---|---|---|---|---|---|
| | 1 | 2 | 3 | 4 | 5 | |
| A0001-01 | 0 | 4 | 15 | 33 | 21 | 3.97 |
| A0001-02 | 4 | 5 | 2 | 1 | 0 | 2.00 |
| A0002-01 | 3 | 8 | 20 | 2 | 0 | 2.64 |
| ⋮ | ⋮ | ⋮ | ⋮ | ⋮ | ⋮ | ⋮ |

FIG.12

| EVALUATION FOR THE PAST ONE YEAR | | PAY RATE |
|---|---|---|
| A | SCORE 4.5 OR MORE | FREE OF CHARGE |
| B | SCORE 4.0 OR MORE | 20% |
| C | SCORE 3.5 OR MORE | 50% |
| D | SCORE LESS THAN 3.5 | 100% |

FIG.13

| | | SCORE | | | |
|---|---|---|---|---|---|
| | | 4.5 OR MORE | 4.0 TO 4.5 | 3.5 TO 4.0 | LESS THAN 3.5 |
| NUMBER OF CASE INFORMATION ITEMS | 50 OR MORE | FREE OF CHARGE | FREE OF CHARGE | FREE OF CHARGE | 20% |
| | 20 TO 50 | FREE OF CHARGE | FREE OF CHARGE | 20% | 50% |
| | 10 TO 20 | FREE OF CHARGE | 20% | 50% | 100% |
| | LESS THAN 10 | 20% | 50% | 100% | 100% |

CASE DATABASE MANAGEMENT SYSTEM AND METHOD

BACKGROUND OF THE INVENTION

1. Field of the Invention

The present invention relates to a case database management system and method, and in particular to a case database management system and method capable of maintaining high quality case information.

2. Description of the Related Art

Japanese Patent Application Laid-Open No. 2005-284846 discloses a diagnostic support system which is configured such that a case image can be registered from a client terminal of each medical facility into a medical database via a database server; the registered case image can be retrieved or referred to at the client terminal of each medical facility; and the case images registered in the medical database can be shared by each medical facility.

In such a diagnostic support system, the case image is recorded by being related to information about a bank account opened by a provider of the case image before the case image provided from each medical facility is registered in a case database. Each time the case image is used, the number of uses is counted to calculate the amount of money according to the number of uses of the case image every predetermined period, and the calculated amount of money is automatically transferred to the bank account opened by the provider of the case image.

However, the system disclosed by Japanese Patent Application Laid-Open No. 2005-284846 has a problem in that although the amount of money according to the number of uses of a case image is transferred to the bank account of the provider of the case image, the system does not provide a method of evaluating whether the referred case image is useful to the user; the system does not provide a sufficient motivation to encourage the user to provide a higher quality case image; and the system cannot be easily used since the database contains wide range of mixes ranging from high quality case images to low quality case images.

In addition, the system has another problem in that the information provided to the user is focused on the image information (case image), and thus text-based case information such as a radiogram interpretation report is not provided, which is not useful enough for a diagnostic support.

SUMMARY OF THE INVENTION

In view of the above circumstances, the present invention has been made to provide a case database management system and method capable of maintaining high quality of case information (case images and diagnostic information corresponding to the case image, and so on) registered in a database, thereby capable of providing the user with useful case information.

In order to achieve the above object, according to a first aspect of the present invention, there is provided a case database management system which is connected to a user terminal via a network and allows the user terminal to refer to necessary case information registered in a database in response to a request from the user terminal, the case database management system comprising: an evaluation information collection device which displays an evaluation input screen on the user terminal to request the user to evaluate the case information registered in the database and collects evaluation information entered on the evaluation input screen; and a case information evaluation device which automatically assigns each case information with an evaluation containing an evaluation point indicating usefulness of the case information based on the evaluation information of each case information collected by the evaluation information collection device.

In other words, the user of the case database management system can evaluate case information registered in the database; and on the other hand, the case database management system collects the evaluation information for each case information item evaluated by the user and assigns each case information item with an evaluation containing an evaluation point indicating usefulness of the case information. Accordingly, for example, if the database contains a plurality of case information items satisfying a search condition, the case database management system can provide the user with case information with high evaluation (high quality case information).

According to a second aspect of the present invention, the case database management system according to the first aspect further includes: an output device which outputs the evaluation assigned to each case information by the case information evaluation device; and a device which manually performs a modification including a deletion of the case information registered in the database in reference to the evaluation assigned to each case information outputted from the output device.

When a third party (for example, a database manager) performs a deletion or the like, the third party can appropriately select case information to be processed by referring to the evaluation assigned to each case information item. This can maintain high quality of case information registered in the database. In addition, this can prevent an erroneous deletion or modification of rare case information to which is seldom referred.

According to a third aspect of the present invention, the case database management system according to the first aspect further include a device which automatically performs a modification including a deletion of the case information registered in the database based on the evaluation assigned to each case information by the case information evaluation device. Thereby it becomes possible to automatically increase the quality of case information accumulated in the database.

According to a fourth aspect of the present invention, the case database management system according to one of the first to third aspects further includes: a case information registration device which receives new case information from the user terminal and registers the case information in the database; and a provider evaluation device which evaluates a provider of the case information based on the evaluation of the case information assigned by the case information evaluation device.

In other words, the case database management system is configured to evaluate the provider who provided case information based on the evaluation assigned to the case information provided by the provider.

According to a fifth aspect of the present invention, the case database management system according to one of the first to third aspects further includes: a case information registration device which receives new case information from the user terminal and registers the case information in the database; a register count management device which counts the number of case information items registered within a predetermined period for each provider of the case information and manages the register count; and a provider evaluation device which evaluates a provider of the case information based on the managed register count and the evaluation of the case information corresponding to the register count provided by the case information evaluation device.

In other words, the case database management system can be configured to evaluate the provider who provided the case information, based on the number of case information items provided by the provider within a predetermined period and the evaluation of the case information corresponding to the register count. For example, the case database management system can be configured such that the more the register count and the more highly evaluated case information provided by the provider, the higher the evaluation of the provider.

According to a sixth aspect of the present invention, the case database management system according to one of the first to fifth aspects further includes an accounting device which manages information about system usage fees for the user who used the case information.

According to a seventh aspect of the present invention, the case database management system according to the forth or the fifth aspect further includes an accounting device which manages information about system usage fees for the user who referred to case information and reflects the evaluation of the provider assigned by the provider evaluation device on the system usage fees of the user.

In other words, the user needs to pay corresponding usage fees before or after the use of the present system, but an information provider (user) assigned high evaluation can get an incentive such as a reduction in usage fees and free of charge, thereby promoting the high quality case information to be provided.

According to an eighth aspect of the present invention, the case database management system according to the fourth or the fifth aspect further includes an information display device which displays, when the user refers to case information at the user terminal, at least one of the evaluation information about the case information to which the user refers, information about the provider who provided the case information, and information about an evaluator who inputted the evaluation information of the case information.

This allows the user to confirm the quality of the case information to which the user refers. For example, the user can confirm whether or not the case information is provided or evaluated by an authority doctor or an authoritative institution.

According to a ninth aspect of the present invention, there is provided a case database management method for allowing a user terminal to refer to necessary case information registered in a database in response to a request from the user terminal, the case database management method comprising: a process of displaying an evaluation input screen on the user terminal to request the user to evaluate the case information registered in the database; a process of collecting via a network evaluation information of the case information entered on the evaluation input screen; and a process of automatically assigning referred case information with an evaluation containing an evaluation point indicating usefulness of the case information based on the evaluation information of the case information collected.

According to a tenth aspect of the present invention, the case database management method according to the ninth aspect further includes: a process of outputting the evaluation assigned to each case information; and a process of manually performing a modification including a deletion of case information registered in the database in reference to the outputted evaluation assigned to each case information.

According to an eleventh aspect of the present invention, the case database management method according to the ninth aspect further includes a process of automatically performing a modification including a deletion of case information registered in the database based on the evaluation assigned to each case information.

According to a twelfth aspect of the present invention, the case database management method according to one of the ninth to eleventh aspects further includes: a process of receiving new case information from the user terminal and registering the case information in the database; and a process of evaluating a provider who provided the case information based on the evaluation assigned to the case information.

According to a thirteenth aspect of the present invention, the case database management method according to one of the ninth to eleventh aspects further includes: a process of receiving new case information from the user terminal and registering the case information in the database; a process of counting the number of case information items registered within a predetermined period for each provider of case information and managing the register count; and a process of evaluating a provider of case information based on the managed register count for the provider and the evaluations assigned to the case information provided by the provider.

According to a fourteenth aspect of the present invention, the case database management method according to the ninth to eleventh aspects further includes a process of managing information about system usage fees for the user who used the case information.

According to a fifteenth aspect of the present invention, the case database management method according to the twelfth or thirteenth aspect further includes a process of managing information about system usage fees for the user who used the case information, the process includes a process of reflecting the evaluation of the provider on the system usage fees of the provider.

According to a sixteenth aspect of the present invention, the case database management method according to the twelfth or thirteenth aspect further includes a process of displaying, when the user refers to case information at the user terminal, at least one of the evaluation information about the case information to which the user refers, information about the provider who provided the case information, and information about an evaluator who inputted the evaluation information of the case information.

According to a seventeenth aspect of the present invention, in the case database management system according to one of the first to the eighth aspects, the case information includes a case image and text-based diagnostic information corresponding to the case image.

According to an eighteenth aspect of the present invention, in the case database management method according to one of the ninth to the sixteenth aspects, the case information includes a case image and text-based diagnostic information corresponding to the case image.

By including a case image and diagnosis information corresponding to the case image in the case information which is registered in the database, it becomes possible for the user to refer to a case image and corresponding text-based diagnostic information such as a radiogram interpretation report when the user refers to the case information.

According to the present invention, the user referring to case information registered in the database is requested to evaluate the case information and the evaluation information is collected by the case information by the case database management system. The case database management system uses the evaluation information collected from the user to evaluate the case information, and thereby maintaining high quality of case information registered in the database and providing the user with high quality case information are accomplished.

BRIEF DESCRIPTION OF THE DRAWINGS

FIG. 2 is a table showing an example of user information stored in a user management DB;

FIG. 3 is a table showing an example of a rate plan for system usage fees determined by a contract with the user;

FIG. 8 shows an example of an evaluation input screen for the user (evaluator) to evaluate case information;

FIG. 9 is a table showing an example of an evaluation record recorded in a case DB;

FIG. 11 is a table showing an example of evaluation records assigned by a manager for each case information item;

FIG. 12 is a table showing an example of a pay rate for the system usage fees to be paid by the user according to the user score; and FIG. 13 is a table showing an example of a pay rate for the system usage fees determined base on the score of the case information and the number of case information items.

DETAILED DESCRIPTION OF THE PREFERRED EMBODIMENTS

Hereinafter, preferred embodiments of the case database management system and method in accordance with the present invention will be described with reference to accompanying drawings.

[Entire System Configuration]

Figure 1:
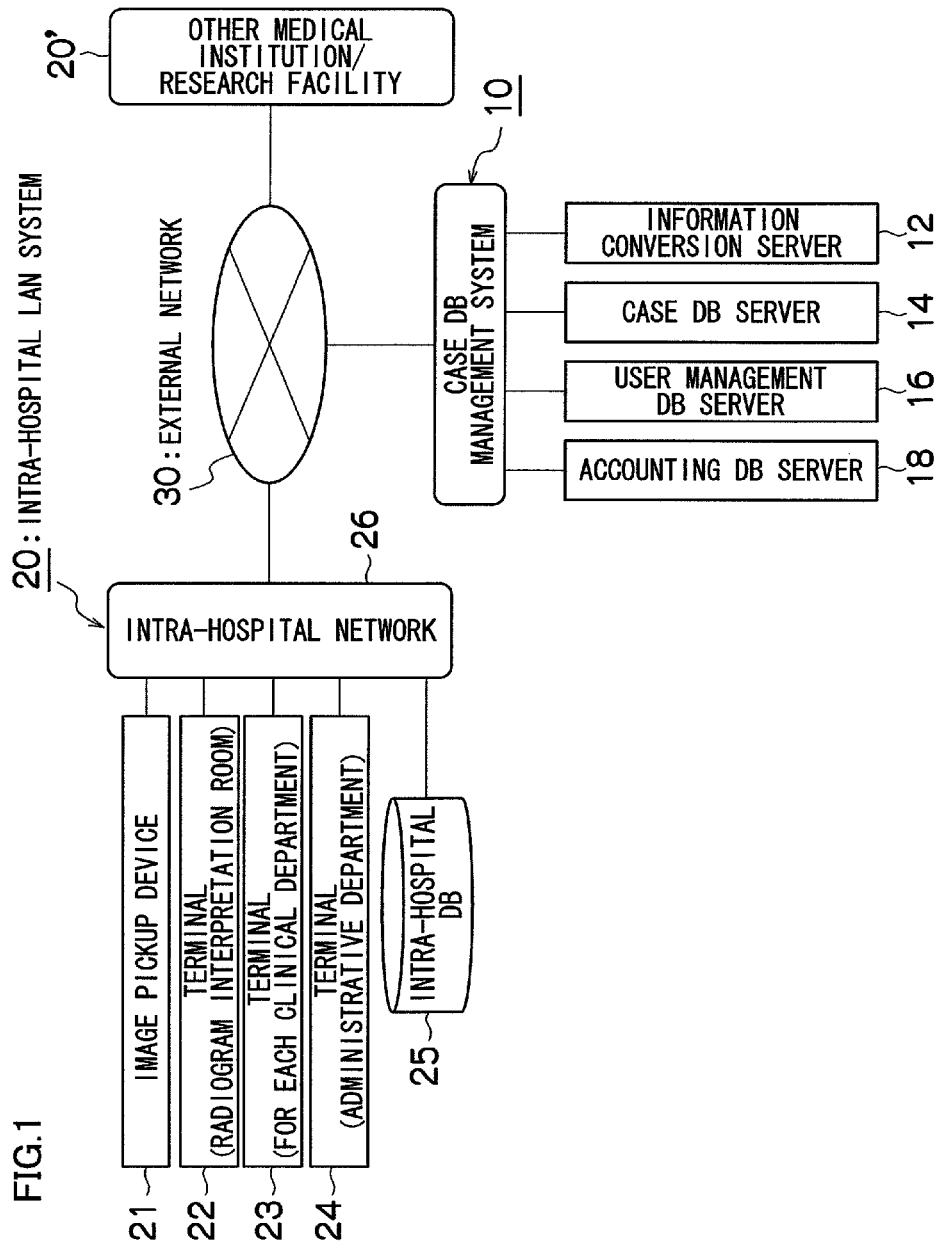
FIG. 1 shows an example of an entire system configuration to which case database management system in accordance with the present invention is applied.

FIG. 1 shows an example of an entire system configuration to which the case database management system in accordance with the present invention is applied.

The system shown in FIG. 1 includes a case database (DB) management system 10 in accordance with the present invention; an intra-hospital local area network (LAN) systems 20 and 20' in a plurality of individual or corporate medical institutions or research facilities; registered user terminals (not shown); and an external network 30 connected to these systems.

The case DB management system 10 includes an information conversion server 12, a case DB server 14, a user management DB server 16, and an accounting DB server 18, each server linked to each other.

The information conversion server 12 checks the content of the case information registered in the case DB described later and corrects inappropriate words and expressions if necessary. Here, the case information includes a diagnostic image (case image) taken by an image pickup device such as an X-ray CT scanner, X-ray equipment and MRI equipment; and text-based diagnostic information such as a radiogram interpretation report created by a radiogram interpreting doctor for the case image and diagnostic content created by a clinician. The information conversion server 12 checks for careless errors in diagnostic information (text content).

A text mining technique for medical application (Toshiba Review, Vol. 60, No. 9, September, 2005) can be used as a technical method for checking the text content. When an ambiguous expression, a contradicting expression, a grammatical error or the like is found, the information conversion server 12 issues an alarm. On the basis of this alarm, the case DB manager stops registering case information in the case DB or makes a correction before performing registering again. If no alarm is issued or an appropriate correction is made in response to the alarm, the case information is registered in the case DB.

This information conversion server 12 can increase the quality of case information registered in the case DB. It should be noted that when an error is found in the text, the information conversion server 12 issues an alarm to prompt the manager for correction, but the information conversion server 12 may automatically correct careless errors.

The case DB server 14 is provided with a case DB and include a function to register in the case DB the case information provided from the user (in this case, the user is an information provider) at a medical institution or the like using the present system; a function to retrieve case information according to the user request from the case information registered in the case DB; and a function to provide the user with the retrieved case information. In addition, the case DB server 14 has functions in accordance with the present invention, including a function to collect evaluation information for case information registered in the case DB from the user; a function to add an evaluation to each case information item based on the collected evaluation information; and a function to evaluate the information provider.

It should be noted that the detail of each function will be described later. In addition, the case DB may contain not only the case information itself, but also another information indicating diagnostic information for use in text search of the case information and a feature quantity of the case image (size, shape, density, and the like of lesioned area); and an index (register destination information) indicating in which intra-hospital DB of medical institution the case information is registered. Alternatively, in the case where the case information is provided from a user of a private hospital without having an intra-hospital DB, the case information itself may be registered in the case DB; and in the case where the case information is provided from a user of a medical institution having an intra-hospital DB, the information necessary for retrieving the case information and the register destination information of the case information may be registered in the case DB.

The user management DB server 16 is provided with a user management DB and stores, in the user management DB, information about an authorized user (registered user) of a medical institution and the like using the present system.

FIG. 2 is a table showing an example of user information stored in the user management DB. As shown in FIG. 2, a numerical value (a value ranging from 0 to 5) indicating an evaluation of the user (information provider) is recorded in column "rank". The case DB server 14 calculates the evaluation of the user according to the quality of case information provided from the user, the detail of which will be described later.

The accounting DB server 18 is provided with an accounting DB and stores, in the accounting DB, information about system usage fees to be paid by the user according to the server 18 system usage state and the like.

FIG. 3 is a table showing an example of a rate plan for system usage fees determined by a contract with the user.

As shown in FIG. 3, the user using the present system needs to pay corresponding usage fees before or after the use of the present system. The usage fees should be paid as an individual or a corporate according to a flat rate or a measured rate.

For the flat rate, the usage fee is determined based on the maximum use period, the maximum number of uses, and the like. For the measured rate, the usage fee is determined based on the variables such as the number of uses, the number of usage days, the quality of reference information and the like.

In addition, the user can get an incentive such as a reduction in the determined usage fees and a free of charge, based on information such as the evaluation of the user and the like managed by the user management DB server 16, the detail of which will be described later. The accounting DB server 18 manages information such as a reduction in usage fees and the like.

The intra-hospital LAN system 20 is configured as an intra-hospital network 26 which connects an image pickup device 21 such as an X-ray CT scanner, X-ray equipment, MRI equipment, or the like; a terminal 22 disposed in a radiogram interpretation room; a terminal 23 disposed for each clinical department; a terminal 24 disposed in an administrative department; and an intra-hospital DB 25.

The diagnostic image taken by the image pickup device 21 is stored in the intra-hospital DB 25 as an image file complying with a standard such as DICOM (Digital Imaging and Communications in Medicine) which has patient identification information (patient ID), and header information containing the date and time the image was taken.

A radiogram interpreting doctor in the radiogram interpretation room accesses the intra-hospital DB 25 from the terminal 22 to read out a diagnostic image; makes the diagnostic image displayed on the monitor; and interprets and diagnoses based on the displayed diagnostic image. Then, the radiogram interpreting doctor inputs a radiogram interpretation report from the terminal 22 and records the diagnostic image associated with the radiogram interpretation report in the intra-hospital DB 25.

An attending physician for each clinical department inputs a patient ID from the terminal 23; reads out the diagnostic image, the radiogram interpretation report, the electronic medical record, and the like of his or her patient from the intra-hospital DB 25; and records the diagnostic content in the electronic medical record in reference to the diagnostic image and the radiogram interpretation report. In addition, the attending physician collects a pathological tissue and the like for a definitive diagnosis and also records the definitive diagnostic result and the like. It should be noted that, in this embodiment, the definitively diagnosed image is referred to as a case image.

A clerk in an administrative department completes various forms such as a medical fee form and an inspection request form by using the terminal 24, and records the forms in the intra-hospital DB 25.

It should be noted that a terminal (not shown) is also installed in a pharmaceutical department which prescribes a medicine. In addition, each terminal in the hospital may have a different access right. For example, the terminal 24 in the administrative department is configured such that an electronic medical record cannot be accessed or even if accessed, information cannot be recorded and so on, in the electronic medical record.

The intra-hospital LAN system 20' in other medical institution/research facility has the same configuration as the intra-hospital LAN system 20.

In order to lower costs of managing the intra-hospital DB, a private hospital and the like can use the present system only by installing a terminal capable of connecting to the external network 30.

A secure network such as IPSec and SSL-VPN is used as the external network 30.

[Registration in the Intra-Hospital DB]

Figure 4:
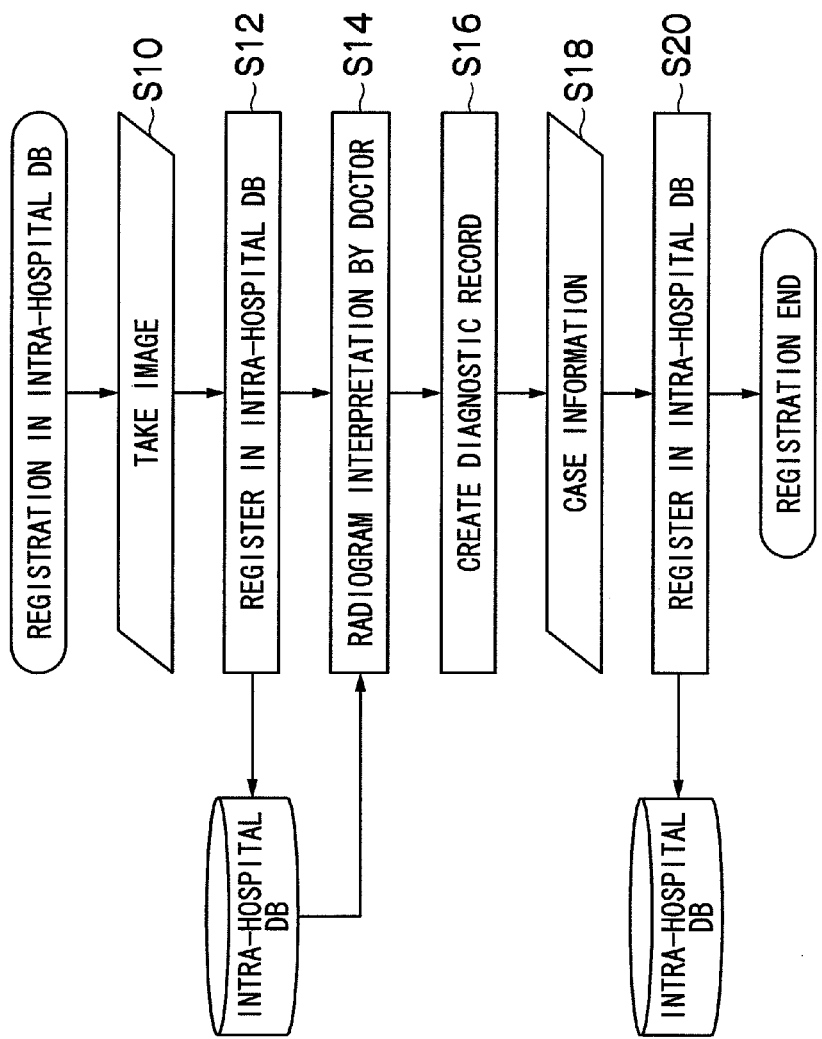
FIG. 4 is a flowchart showing a procedure for taking a diagnostic image and registering the image in an intra-hospital DB.

Next, the procedure for taking a diagnostic image and registering the diagnostic image in the intra-hospital DB will be described with reference to the flowchart shown in FIG. 4.

Each medical institution takes an image of a patient by the image pickup device 21 (step S10). The taken diagnostic image is registered in the intra-hospital DB (step S12). Afterward, a radiogram interpreting doctor or an attending physician for each clinical department performs a diagnosis of the diagnostic image (step S14), and then creates a radiogram interpretation report and an electronic medical record (diagnostic record) (step S16). Finally, the case information (case image plus diagnostic information) composed of the definitively diagnosed image (case image) and text-based diagnostic information such as a radiogram interpretation report and a findings report at definitive diagnosis is registered again in the intra-hospital DB (steps S18 and S20).

[Registration in Case DB]

Figure 5:
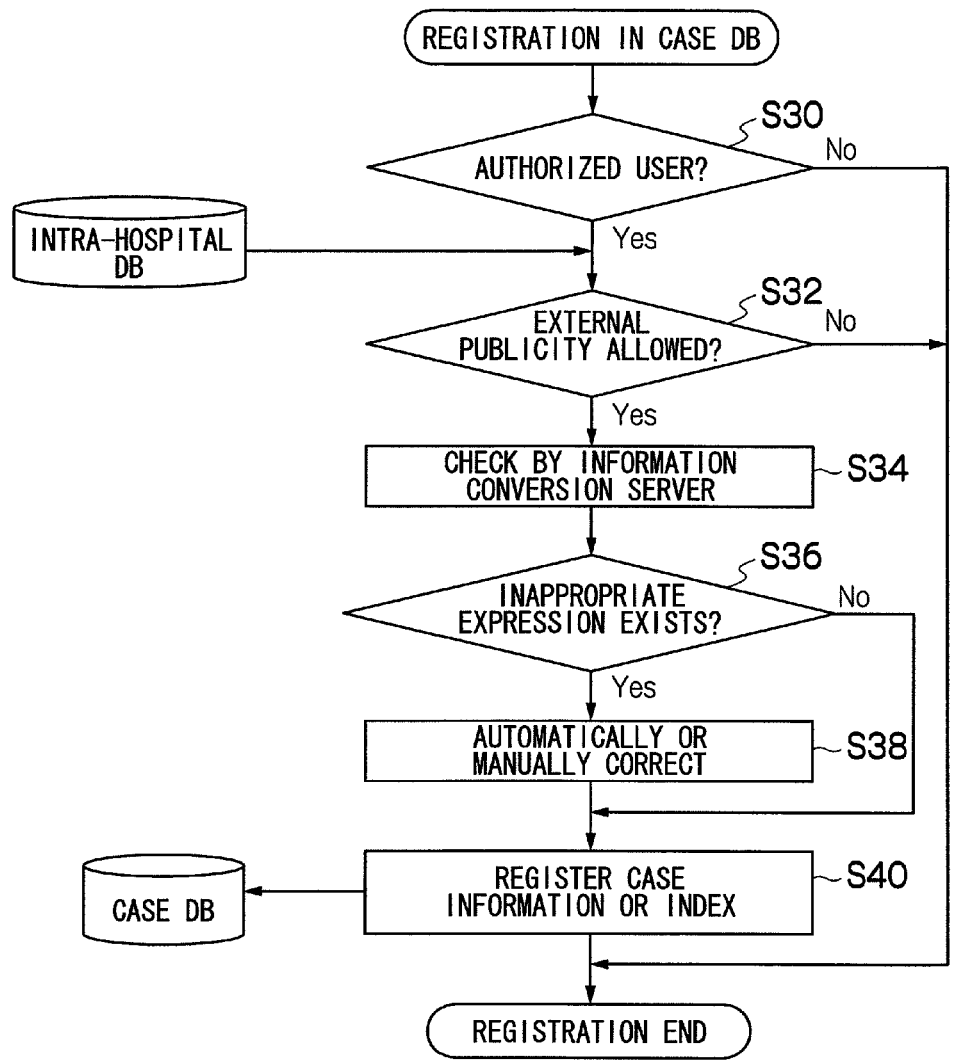
FIG. 5 is a flowchart showing a procedure for registering case information in an intra-hospital DB of each medical institution into a case DB in a case DB server.

Next, the procedure for registering case information in an intra-hospital DB of each medical institution into the case DB in the case DB server 14 will be described with reference to the flowchart shown in FIG. 5.

Case information created in each medical institution is registered in the case DB so as to share the case information with external institutions.

Preliminarily, the user of the present system is registered as a user in the case DB management system 10 in units of individual or corporate, and the user information is registered in the user management DB of the user management DB server 16.

The user management DB server 16 determines whether or not the user who provides case information (information provider) is authorized (step S30). The determination can be performed by comparing the user ID, the password, the source IP address, and the like input through the terminal with the information preliminarily recorded in the user management DB.

When authenticated as an authorized user, the information provider uploads the case information allowed to be opened to the public (step S32: Yes) from among the case information registered in the intra-hospital DB, from the terminal to the case DB management system 10. The uploaded case information is sent to the information conversion server 12, where a simple check is performed (step S34).

More specifically, the information conversion server 12 checks the content of the text-based diagnostic information contained in the case information to be registered. If an ambiguous expression, a contradictory expression, a grammatical error, or the like is found in the text, the information conversion server 12 automatically corrects the error, or issues an alarm to prompt the case DB manager to manually correct the error (steps S36 and S38).

The case information checked by the information conversion server 12 is passed to the case DB server 14, and then the case DB server 14 registers the case information in the case DB (step S40). It should be noted that the case image in the case information may be replaced with an index indicating in which intra-hospital DB of medical institution the case information is registered.

[Reference to Case Information]

The registered user can refer to the required case information by sending a reference request from the user terminal to the case DB server 14.

Figure 6:
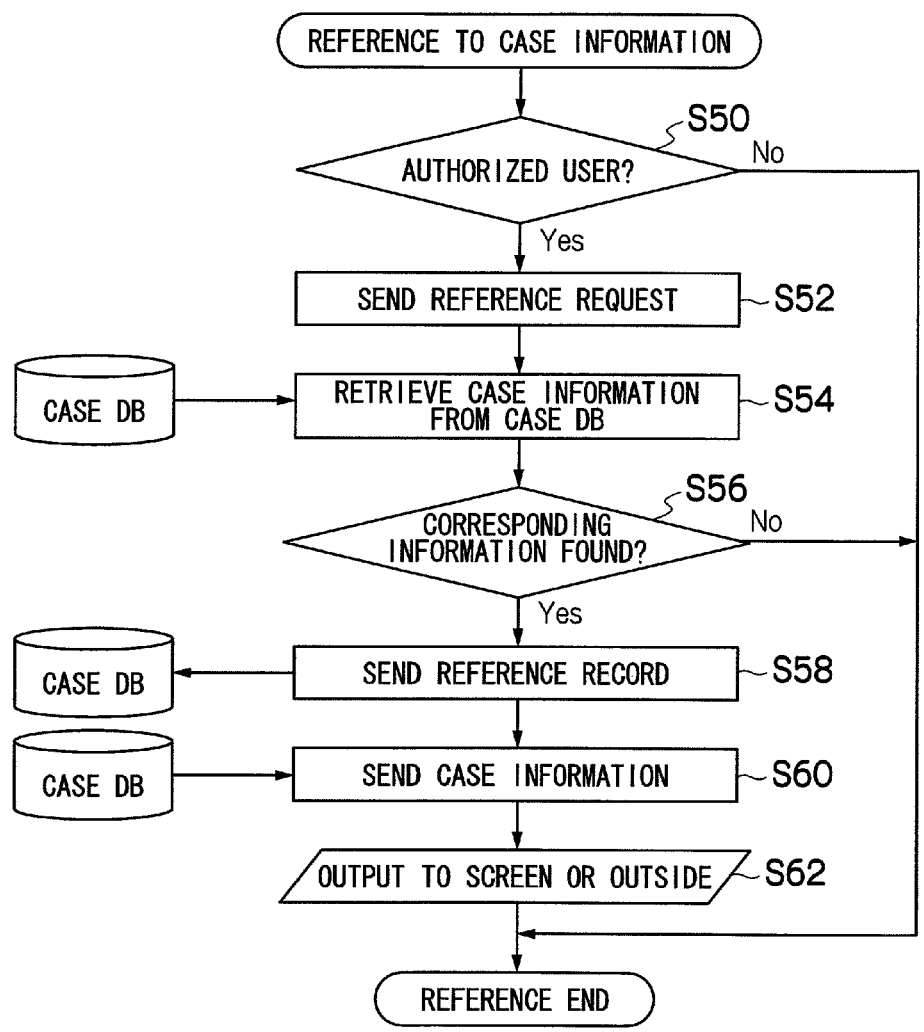
FIG. 6 is a flowchart showing a procedure for referring to case information registered in the case DB.

FIG. 6 is a flowchart showing a procedure for referring to case information stored in the case DB.

In the same manner as for the registration of case information in the case DB, a user registration is required in advance for the user to refer to case information.

The user management DB server 16 determines whether or not the user is authorized to refer to the case information (step S50). When authenticated as an authorized user, the user can retrieve or refer to case information registered in the case DB.

The authorized user sends a reference request from the user terminal to the case DB server 14 (step S52). This reference request contains keyword information required for search. If the user wants to refer to a similar case image, a diagnostic image may also be sent.

When the reference request is received, the case DB server 14 retrieves the case information corresponding to the reference request from the case DB (step S54).

If the corresponding case information is not found, the reference termination process is performed; and if the corresponding case information is found, the reference record is sent to the case DB to update the reference record of the case DB (step S58). It should be noted that the reference record is a log indicating when and which image the user referred to. An analysis of this log can reveal the number of user references and which image is frequently referred to. The number of user references can be used for accounting; and the frequently referred image can be used as information to be added at case information evaluation.

Subsequently, the corresponding case information is read from the case DB and sent to the user terminal (step S60).

The sent case information is displayed on a screen of the user terminal, on which the user can refer to the displayed case information (step S62).

This embodiment is configured such that first the case information registered in an external case DB is referred to, but without being limited to this. For example, first, the case information registered in the intra-hospital DB is referred to and if appropriate case information is not found, the case information registered in an external case DB may be referred to.

In addition, if a plurality of case information items corresponding to the reference request are retrieved, there may be a method of sending the plurality of case information items in descending order of evaluation; a method of sending the plurality of case information items in random order; and a method of sending a list of case information items to the user terminal and requesting the user to select one. In addition, the information which can be referred to may contain not only the above case information, but also information about the provider of the case information, an evaluation assigned to the case information, information about the evaluator of the case information, a related case (similar disease), and medical information.

[Evaluation of Case Information (User Side)]

Hereinafter, the method for the user to evaluate the case information referred to by the user.

Figure 7:
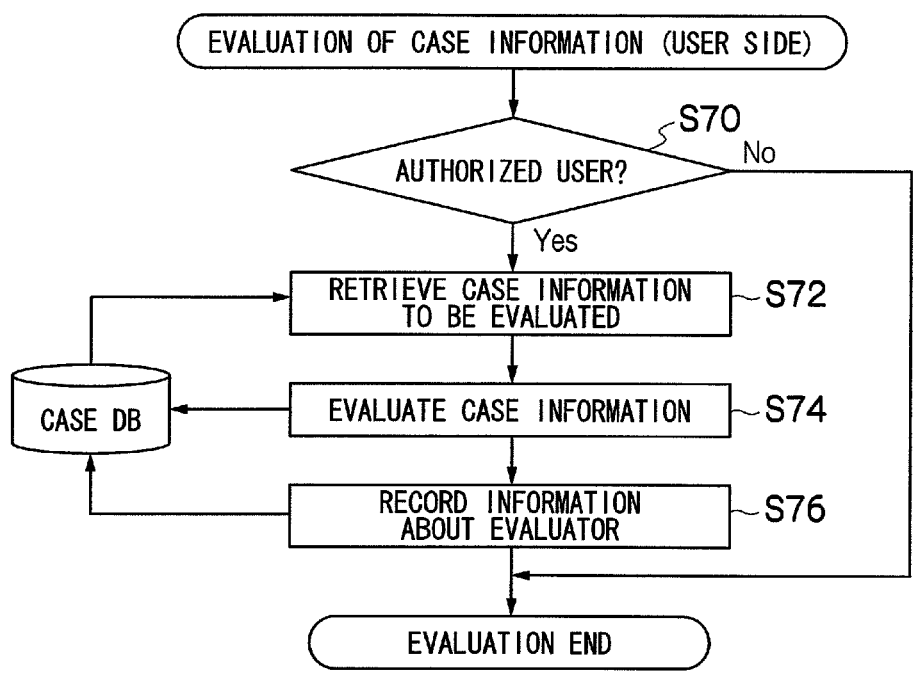
FIG. 7 is a flowchart showing a procedure for evaluating the case information referred to by the user.

FIG. 7 is a flowchart showing a procedure for evaluating the case information referred to by the user.

The user management DB server 16 determines whether or not the user (evaluator) is authorized to evaluate the case information (step S70). When authenticated as an authorized user, the user can evaluate the case information referred to by the user.

The authorized user retrieves the case information to be evaluated (step S72). The retrieval of the case information to be evaluated can be performed in the same manner as for the retrieval of the case information to be referred to. When retrieved, the case information to be evaluated is sent to the terminal of the evaluator. Additionally, an evaluation input format as shown in FIG. 8 is also sent to the terminal of the evaluator.

The sent case information and evaluation input format are displayed on the screen of the terminal of the evaluator. The evaluator enters an evaluation of the case information to be evaluated on a screen of the evaluation input format (evaluation input screen) by referring to the displayed case information to be evaluated (step S74).

In this embodiment, as shown in FIG. 8, the user is asked to select one by five-point evaluation (5: very useful, 4: useful, 3: middle, 2: not much useful, 1: not useful) for the case information to be evaluated and if necessary, write a comment.

The information about the evaluator of the case information assigned to the case information to be evaluated as described above (evaluation information) is sent to the case DB management system 10 and recorded in the case DB (step S76).

FIG. 9 is a table showing an example of an evaluation record recorded in the case database.

As shown in FIG. 9, each time the evaluator evaluates the case information, the evaluation date, the evaluation time, the evaluated case ID, (case information ID), the evaluator ID (user ID), the evaluation (a numerical value based on the five-point evaluation), the source IP address, and the like are recorded. Since information about the evaluator is recorded, a biased evaluation input can be prevented.

It should be noted that this evaluation record is not opened to the public. In addition, this embodiment is configured such that the user can evaluate the case information any time, but the present invention is not limited to this. The system may be configured such that the user may evaluate the case information when the user refers to the case information as shown in FIG. 6; and further alternatively, the user may be required to evaluate the case information when the user refers to the case information.

[Evaluation of Case Information (Manager Side) and Evaluation of the User]

Hereinafter, the method for the manager side of the present system to evaluate each case information item registered in the case DB; to evaluate the user; and to reflect the evaluation result on the system will be described.

Figure 10:
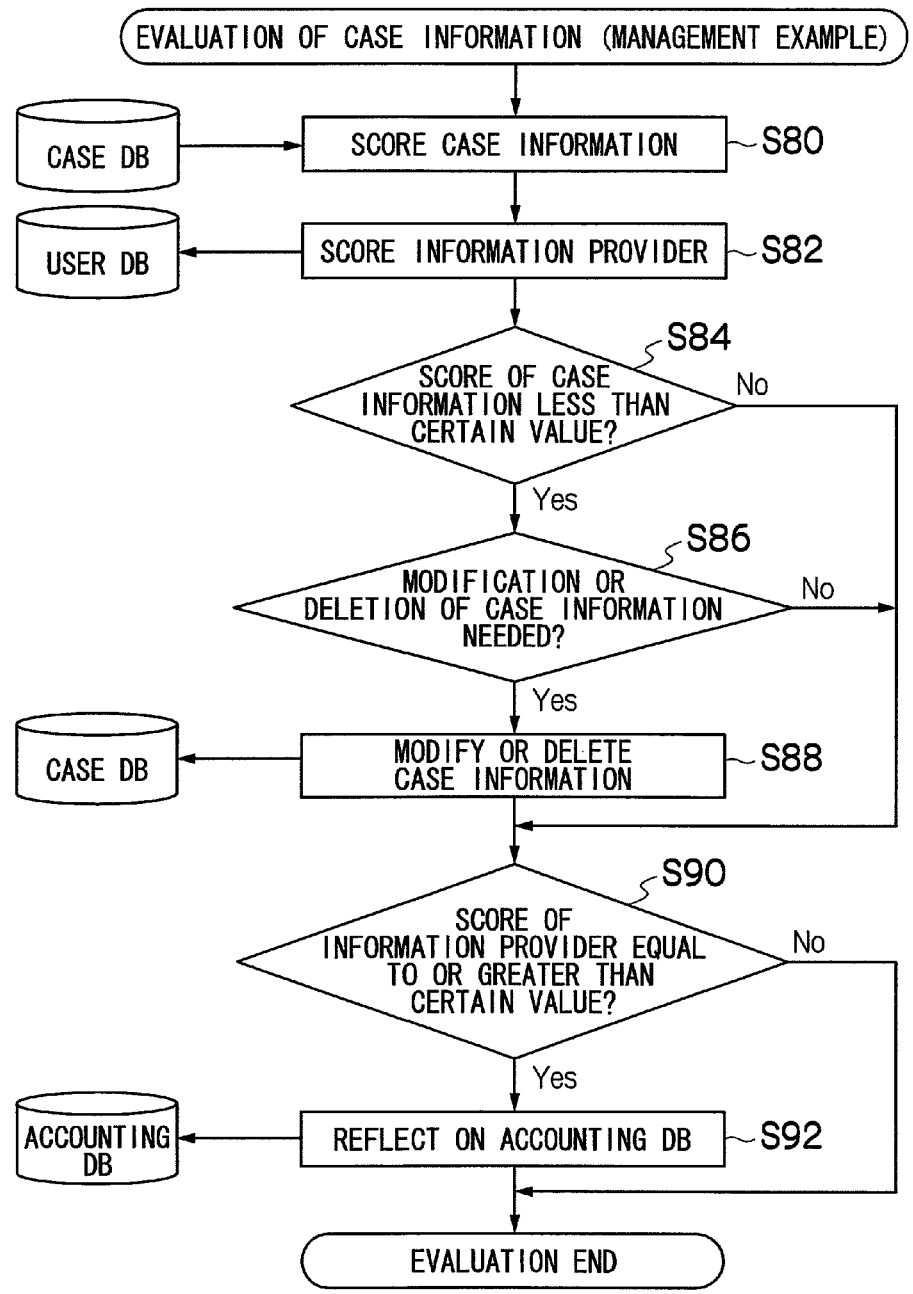
FIG. 10 is a flowchart showing a procedure for reflecting the evaluation result of each case information item and the user on the system.

FIG. 10 is a flowchart explaining the method of reflecting the evaluation results of the case information and the user on the system. It should be noted that the evaluation of the case information and the user is performed periodically (for example every month).

As shown in FIG. 10, the case DB server 14 calculates a score for the case information based on the evaluation record (see FIG. 9) recorded in the case DB, using the evaluations assigned by the user for each case information item according to the following formula 1 (step S80).

$$\text{Score} = [5 \times (\text{number of evaluations of 5 points}) + 4 \times (\text{number of evaluations of 4 points}) + 3 \times (\text{number of evaluations of 3 points}) + 2 \times (\text{number of evaluations of 2 points}) + 1 \times (\text{number of evaluations of 1 point})] / (\text{Total number of evaluations}) \quad (\text{Formula 1})$$

The above formula 1 calculates the average of five-point evaluations assigned by the user. It should be noted that the scoring method for case information is not limited to this embodiment. Additionally, the number of evaluations assigned by the user may be limited to the most recent predetermined number of evaluations. Further, for rare case information, a five-point evaluation result may be weighted.

FIG. 11 is a table showing an example of an evaluation record assigned by the manager side for each case information item. The evaluation of case information is not limited to the above scoring, but may contain not only the score but also other factors (such as a comment of the evaluator).

Subsequently, the provider (user) providing the case information is evaluated (scored) and the evaluation of the user is recorded in the user management DB server (step S82). A case information which is assigned a high evaluation (score) is determined as useful information and a higher evaluation (score) is also assigned to the information provider who provided the case information (see "Rank" in FIG. 3).

Next, a determination is made whether or not the score of the case information registered in the case DB is less than a certain value (step S84). If the score of the case information is not less than the certain value (equal to or greater than the certain value), the process goes to step S90 without performing processes S86 and S88.

On the other hand, if the score of the case information is less than the certain value, a third party (for example, the system manager) determines whether or not the modification or deletion of the case information is needed (step S86). It should be noted that rare case information is seldom evaluated, and thus the evaluation is not fixed; and the evaluation of the case information with a short storage period or with a small number of evaluations is not fixed either. In view of these problems, the third party needs to determine whether or not the modification or deletion of the case information is needed. This can prevent an erroneous modification or deletion of the rare case information.

If the determination is made that the modification or deletion of the case information is needed, the third party or another third party with a permission from the information provider modifies or deletes the case information (especially diagnostic information) registered in the case DB by using an operation device such as a keyboard of the case DB server 14 (step S88). This can maintain high quality of case information registered in the case DB.

It should be noted that in the above embodiment, the third party finally determines whether or not the modification or deletion of the case information is needed, but the present invention is not limited to this embodiment. The determination may be automatically made, based on the score of the case information registered in the case DB, whether or not the modification or deletion of the case information is needed; and the case information satisfying a predetermined condition may be automatically deleted. This can automatically organize the case information in the case DB.

Next, a determination is made whether or not the score assigned to the system user (information provider) is equal to or greater than a certain value (step S90). If the score is equal to or greater than the certain value, the case DB management system reflects the score on the system usage fees to be paid by the user (step S92).

FIG. 12 is a table showing an example of a pay rate for the system usage fees to be paid by the user according to the score assigned to the user (the user score).

As shown in FIG. 12, if the score assigned to the user is less than 3.5, the user should pay in full (100%); if the score is 3.5 or more and less than 4.0, the user should pay in half (50%); if the score is 4.0 or more and less than 4.5, the user should pay 20%; and if the score is 4.5 or more, the user should pay none.

Since the score assigned to the user is based on the evaluation of the case information provided by the user, an information provider who provided one case information item assigned a high evaluation is more favorable than an information provider who provided many case information items assigned a mix of high and low evaluations. Accordingly, preferably the information provider is evaluated by considering the quality (score) of case information provided by the provider and the number of case information items provided by the provider in a predetermined period (for example, one year).

FIG. 13 is a table showing an example of a pay rate for the system usage fees determined base on the score of the case information and the number of case information items.

As shown in FIG. 13, the pay rate is determined such that the higher the score of the case information provided by the information provider and the more the number of case information items provided by the information provider, the less the system usage fees to be paid by the information provider.

The pay rate for the system usage fees for each user is determined as described above and recorded in the accounting DB. As the method of reflecting the evaluation of the information provider on the system usage fees, not only the above pay rate, but also a predetermined discount price, an extended period of system usage, or the like may be considered.

As described above, the case DB management system reflects the quality and the amount of case information provided by a user on the system usage fees to be paid by the user, and thus the system can encourage the user to provide higher quality and more number of case information items, thereby activating the entire system.

[Modification]

The case DB management system in accordance with the present invention may be configured as a system which is used only internally such as in a research facility or a medical institution. In this case, there is no need to evaluate the information provider (user) or to reflect the evaluation on the system usage fees.

In addition, there is a security problem in that if the intrahospital DB can be referred to from outside, to what extent the reference is allowed. Therefore, preferably a public open DB server is stalled in a demilitarized zone (DMZ) or all case information is registered in the case DB outside the hospital.

Further, for the case where the same user uses the case information which the user has previously referred to, when the system charge a system usage fees to the user, a re-accounting, a discount, a free of charge for a predetermined period, or the like may be considered. In addition, when case information is referred to, a thumbnail view of a case image, an excerpt of diagnostic information and so on for the case information may be offered for free; and an entire case image and a full text of diagnostic information and so on for the case information may be offered for a fee. For example, the above free-of-charge information may be used such that when a plurality of case information items are retrieved in response to a reference request, a list of thumbnail views of case images and excerpts of diagnostic information items are displayed for the user to select a desired case information item.

In addition, in order to prevent a secondary use of case information, for example, protection by watermarking may be used and/or downloading may be disabled (screen display and printing are permitted).

Further, except the use inside the same hospital, when an information provider uploads case information or a user refers to case information, an encryption or the like is performed on any private information identifying an individual person to be anonymized.

What is claimed is:

1. A case database management system which is connected to a plurality of user terminals via a network and allows the user terminals to refer to case information registered in a database in response to a request from the user terminals, the case database management system comprising:
  a case information registration device which receives a plurality of case information items including the case information from the user terminals, and registers the plurality of case information items in the database, wherein the case information comprises a case image, that is a definitively diagnosed diagnostic image, and text-based diagnostic information corresponding to the case image;
  an evaluation information collection device which displays an evaluation input screen on the user terminal to request a plurality of users to evaluate the case information registered in the database and collects a plurality of pieces of evaluation information entered on the evaluation input screen;
  a case information evaluation device which automatically assigns the case information with an evaluation containing an evaluation point indicating usefulness of the case information based on the pieces of evaluation information about the case information collected by the evaluation information collection device;
  an output device which outputs the evaluation assigned to the case information by the case information evaluation device; and
  a device which receives information from a database manager to manually perform modification including deletion of the case information registered in the database in reference to the evaluation assigned to the case information outputted from the output device,
  wherein the evaluation includes an average value of evaluation points from the users who referred to the case information, further comprising:
  a register count management device which counts a number of the plurality of case information items registered within a predetermined period for a provider of the case information and manages the register count; and
  a provider evaluation device which evaluates the provider of the case information based on the managed register count and the evaluation of the case information corresponding to the register count provided by the case information evaluation device.

2. The case database management system according to claim 1, further comprising
  an accounting device which manages information about system usage fees for the users who use the case information.

3. A case database management system which is connected to a plurality of user terminals via a network and allows the user terminals to refer to case information registered in a database in response to a request from the user terminals, the case database management system comprising:
  a case information registration device which receives a plurality of case information items including the case information from the user terminals, and registers the plurality of case information items in the database, wherein the case information comprises a case image, that is a definitively diagnosed diagnostic image, and text-based diagnostic information corresponding to the case image;
  an evaluation information collection device which displays an evaluation input screen on the user terminal to request a plurality of users to evaluate the case information registered in the database and collects a plurality of pieces of evaluation information entered on the evaluation input screen;
  a case information evaluation device which automatically assigns the case information with an evaluation containing an evaluation point indicating usefulness of the case information based on the pieces of evaluation information about the case information collected by the evaluation information collection device;
  an output device which outputs the evaluation assigned to the case information by the case information evaluation device; and
  a device which receives information from a database manager to manually perform modification including deletion of the case information registered in the database in reference to the evaluation assigned to the case information outputted from the output device,
  wherein the evaluation includes an average value of evaluation points from the users who referred to the case information,
  a provider evaluation device which evaluates a provider of the case information based on the evaluation of the case information assigned by the case information evaluation device, and further comprising
  an accounting device which manages information about system usage fees for the users who refer to the case information and reflects the evaluation of the provider assigned by the provider evaluation device on the system usage fees of the users.

4. The case database management system according to claim 3, further comprising
  an information display device which displays, when the users refer to the case information at the user terminal, at least one of the evaluation information about the case information to which the users refer, information about the provider of the case information, and information about an evaluator who inputs the evaluation information about the case information.

5. A case database management method for allowing a plurality of user terminals to refer to case information registered in a database in response to a request from the user terminals, the case database management method comprising:
  receiving a plurality of case information items including the case information from the user terminals, and registering the plurality of case information items in the database, wherein the case information comprises a case image, that is a definitively diagnosed diagnostic image, and text-based diagnostic information corresponding to the case image;
  displaying an evaluation input screen on the user terminal to request a plurality of users to evaluate the case information registered in the database;
  collecting via a network a plurality of pieces of evaluation information of the case information entered on the evaluation input screen; and
  automatically assigning the case information with an evaluation containing an evaluation point indicating usefulness of the case information based on the pieces of evaluation information about the case information collected;

outputting the evaluation assigned to the case information;

manually performing modification including deletion of case information registered in the database in reference to the evaluation assigned to the case information, wherein the evaluation includes an average value of evaluation points from the users who referred to the case information, and further comprising:

counting a number of the plurality of case information items registered within a predetermined period for a provider of the case information and managing the register count; and evaluating the provider of the case information based on the managed register count for the provider and the evaluations assigned to the case information provided by the provider.

6. The case database management method according to claim 5, further comprising managing information about system usage fees for the users who use the case information.

7. A case database management method for allowing a plurality of user terminals to refer to case information registered in a database in response to a request from the user terminals, the case database management method comprising:

receiving a plurality of case information items including the case information from the user terminals, and registering the plurality of case information items in the database, wherein the case information comprises a case image, that is a definitively diagnosed diagnostic image, and text-based diagnostic information corresponding to the case image;

displaying an evaluation input screen on the user terminal to request a plurality of users to evaluate the case information registered in the database;

collecting via a network a plurality of pieces of evaluation information of the case information entered on the evaluation input screen; and automatically assigning the case information with an evaluation containing an evaluation point indicating usefulness of the case information based on the pieces of evaluation information about the case information collected;

outputting the evaluation assigned to the case information; and manually performing modification including deletion of case information registered in the database in reference to the evaluation assigned to the case information, wherein the evaluation includes an average value of evaluation points from the users who referred to the case information, and evaluating a provider who provides the case information based on the evaluation assigned to the case information, and further comprising managing information about system usage fees for the users who use the case information, and reflecting the evaluation of the provider on the system usage fees of the provider.

8. The case database management method according to claim 7, further comprising displaying, when the users refer to the case information at the user terminal, at least one of the evaluation information about the case information to which the users refer, information about the provider who provided the case information, and information about an evaluator who input the evaluation information of the case information.

9. A case database management system which is connected to a plurality of user terminals via a network and allows the user terminals to refer to case information registered in a database in response to a request from the user terminals, the case database management system comprising:

a case information registration device which receives a plurality of case information items including the case information from the user terminals, and registers the plurality of case information items in the database, wherein the case information comprises a case image, that is a definitively diagnosed diagnostic image, and text-based diagnostic information corresponding to the case image;

an evaluation information collection device which displays an evaluation input screen on the user terminal to request a plurality of users to evaluate the case information registered in the database and collects a plurality of pieces of evaluation information entered on the evaluation input screen;

a case information evaluation device which automatically assigns the case information with an evaluation containing an evaluation point indicating usefulness of the case information based on the pieces of evaluation information about the case information collected by the evaluation information collection device;

a device which automatically performs modification including deletion of the case information registered in the database based on the evaluation assigned to the case information by the case information evaluation device, wherein the evaluation includes an average value of evaluation points from the users who referred to the case information, and further comprising:

a register count management device which counts a number of the plurality of case information items registered within a predetermined period for a provider of the case information and manages the register count; and a provider evaluation device which evaluates the provider of the case information based on the managed register count and the evaluation of the case information corresponding to the register count provided by the case information evaluation device.

10. A case database management system which is connected to a plurality of user terminals via a network and allows the user terminals to refer to case information registered in a database in response to a request from the user terminals, the case database management system comprising:

a case information registration device which receives a plurality of case information items including the case information from the user terminals, and registers the plurality of case information items in the database, wherein the case information comprises a case image, that is a definitively diagnosed diagnostic image, and text-based diagnostic information corresponding to the case image;

an evaluation information collection device which displays an evaluation input screen on the user terminal to request a plurality of users to evaluate the case information registered in the database and collects a plurality of pieces of evaluation information entered on the evaluation input screen;

a case information evaluation device which automatically assigns the case information with an evaluation containing an evaluation point indicating usefulness of the case information based on the pieces of evaluation information about the case information collected by the evaluation information collection device;

a device which automatically performs modification including deletion of the case information registered in the database based on the evaluation assigned to the case information by the case information evaluation device, wherein the evaluation includes an average value of evaluation points from the users who referred to the case information, and further comprising:

a provider evaluation device which evaluates a provider of the case information based on the evaluation of the case information assigned by the case information evaluation device; and an accounting device which manages information about system usage fees for the users who refer to the case information and reflects the evaluation of the provider assigned by the provider evaluation device on the system usage fees of the users.

11. A case database management method for allowing a plurality of user terminals to refer to case information registered in a database in response to a request from the user terminals, the case database management method comprising:

receiving a plurality of case information items including the case information from the user terminals, and registering the plurality of case information items in the database, wherein the case information comprises a case image, that is a definitively diagnosed diagnostic image, and text-based diagnostic information corresponding to the case image;

displaying an evaluation input screen on the user terminal to request a plurality of users to evaluate the case information registered in the database;

collecting via a network a plurality of pieces of evaluation information of the case information entered on the evaluation input screen; and automatically assigning the case information with an evaluation containing an evaluation point indicating usefulness of the case information based on the pieces of evaluation information about the case information collected;

automatically performing modification including deletion of the case information registered in the database based on the evaluation assigned to the case information, wherein the evaluation includes an average value of evaluation points from the users who referred to the case information and further comprising:

counting a number of the plurality of case information items registered within a predetermined period for a provider of the case information and managing the register count; and evaluating the provider of the case information based on the managed register count for the provider and the evaluations assigned to the case information provided by the provider.

12. A case database management method for allowing a plurality of user terminals to refer to case information registered in a database in response to a request from the user terminals, the case database management method comprising:

receiving a plurality of case information items including the case information from the user terminals, and registering the plurality of case information items in the database, wherein the case information comprises a case image, that is a definitively diagnosed diagnostic image, and text-based diagnostic information corresponding to the case image;

displaying an evaluation input screen on the user terminal to request a plurality of users to evaluate the case information registered in the database;

collecting via a network a plurality of pieces of evaluation information of the case information entered on the evaluation input screen; and automatically assigning the case information with an evaluation containing an evaluation point indicating usefulness of the case information based on the pieces of evaluation information about the case information collected;

automatically performing modification including deletion of the case information registered in the database based on the evaluation assigned to the case information, wherein the evaluation includes an average value of evaluation points from the users who referred to the case information, and further comprising:

evaluating a provider who provides the case information based on the evaluation assigned to the case information; and managing information about system usage fees for the users who use the case information, and reflecting the evaluation of the provider on the system usage fees of the provider.

* * * * *